(12) United States Patent
Wu et al.

(10) Patent No.: US 7,271,004 B2
(45) Date of Patent: Sep. 18, 2007

(54) TRANSGENIC EXPRESSION OF A PHYTOCHROME A GENE

(75) Inventors: Ray J. Wu, Ithaca, NY (US); Ajay K. Garg, Ithaca, NY (US); Ju-Kon Kim, Kyonggi-Do (KR)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/834,786

(22) Filed: Apr. 29, 2004

(65) Prior Publication Data
US 2004/0268443 A1 Dec. 30, 2004

Related U.S. Application Data

(60) Provisional application No. 60/466,528, filed on Apr. 29, 2003.

(51) Int. Cl.
*A01H 5/00* (2006.01)
*A01H 5/10* (2006.01)
*C12N 15/82* (2006.01)
*C12N 5/04* (2006.01)

(52) U.S. Cl. .............. 435/468; 800/298; 800/290; 800/320.2

(58) Field of Classification Search .............. 800/298, 800/290, 295, 278; 435/419, 320.1, 468; 536/23.1, 23.6
See application file for complete search history.

(56) References Cited

U.S. PATENT DOCUMENTS

| 5,656,496 A | 8/1997 | Quail et al. | |
|---|---|---|---|
| 5,945,579 A * | 8/1999 | Smith | 800/298 |
| 6,750,380 B1 * | 6/2004 | Johal et al. | 800/295 |
| 6,875,610 B2 * | 4/2005 | Higginbotham et al. | 435/457 |

FOREIGN PATENT DOCUMENTS

| EP | 0 354 687 A1 | 2/1990 |
|---|---|---|
| WO | WO 02/46425 A1 | 6/2002 |

OTHER PUBLICATIONS

Weller et al. Plant Physiol. 1997. vol. 114, pp. 1225-1236.*
Kyozuka et al. 1993. vol. 102, pp. 991-1000.*
Jain et al., Plant Cell Rep., 1996, vol. 15, pp. 963-968.*
Boylan et al., "Phytochrome A Overexpression Inhibits Hypocotyl Elongation in Transgenic *Arabidopsis*," *Proc. Natl. Acad. Sci. USA* 88: 10806-10810 (1991).
Boylan et al., "Oat Phytochrome is Biologically Active in Transgenic Tomatoes," *Plant Cell* 1:765-773 (1989).
Casal, J.J., "Phytochrome A Enhances the Promotion of Hypocotyl Growth Caused by Reductions in Levels of Phytochrome B in Its Far-Red-Light-Absorbing Form in Light-Grown *Arabidopsis thaliana*," *Plant Physiol.* 112:965-973 (1996).

Clack et al., "The Phytochrome Aproprotein Family in *Arabidopsis* is Encoded by Five Genes: The Sequences and Expression of *PHYD* and *PHYE*," *Plant Mol. Biol.* 25:413-427 (1994).
Clough et al., "Expression of Functional Oat Phytochrome A in Transgenic Rice," *Plant Physiol.* 109:1039-1045 (1995).
Garg et al., "Trehalose Accumulation in Rice Plants Confers High Tolerance Levels to Different Abiotic Stresses," *Proc. Natl. Acad. Sci. USA* 99(25):15898-15903 (2002).
Hiei et al., "Efficient Transformation of Rice (*Oryza sativa* L.) Mediated by *Agrobacterium* and Sequence Analysis of the Boundaries of the T-DNA," *Plant J.* 6(2):271-282 (1994).
Komari et al., "Vectors Carrying Two Separate T-DNAs for Co-Transformation of Higher Plants Mediated by *Agrobacterium tumefaciens* and Segregation of Transformants Free from Selection Markers," *Plant J.* 10(1):165-174 (1996).
Kyozuka et al., "Light-Regulated and Cell-Specific Expression of Tomato *rbcS-gusA* and Rice *rbcS-gusA* Fusion Genes in Transgenic Rice," *Plant Physiol.* 102:991-1000 (1993).
Martinez-Hernandez et al., "Functional Properties and Regulatory Complexity of a Minimal *RBCS* Light-Responsive Unit Activated by Phytochrome, Cryptochrome, and Plastid Signal," *Plant Physiol.* 128:1223-1233 (2002).
Mathews et al., "The Phytochrome Gene Family in Grasses (Poaceae): A Phylogeny and Evidence that Grasses Have a Subset of the Loci Found in Dicot Angiosperms," *Mol. Biol. Evol.* 13:1141-1150 (1996).
Quail et al., "Phytochromes: Photosensory Perception and Signal Transduction," *Science* 268:675-680 (1995).
Quail, P.H., "Phytochrome Photosensory Signalling Networks," *Nat. Rev. Mol. Cell Biol.* 3:85-93 (2002).
Roy et al., "Arginine Decarboxylase Transgene Expression and Analysis of Environmental Stress Tolerance in Transgenic Rice," *Plant Sci.* 160:869-875 (2001).
Smith, H., "Phytochromes and Light Signal Perception by Plants-An Emerging Synthesis," *Nature* 407:585-591 (2001).
Takano et al., "Isolation and Characterization of Rice Phytochrome A Mutants," *Plant Cell* 13:521-534 (2001).
Kong et al., "Characterization of Sunlight-Grown Transgenic Rice Plants Expressing *Arabidopsis* Phytochrome A," *Molecular Breeding* 14:35-45 (2004).
Robson et al., "Genetic Engineering of Harvest Index in Tobacco Through Overexpression of a Phytochrome Gene," *Nature Biotech.* 14:995-998 (1996).

* cited by examiner

Primary Examiner—Ashwin Mehta
(74) Attorney, Agent, or Firm—Nixon Peabody LLP

(57) ABSTRACT

An isolated nucleic acid construct including a nucleic acid molecule encoding a light-labile, phytochrome A, a light-inducible promoter which is 5' to the nucleic acid molecule encoding a light-labile, phytochrome A, and a terminator region which is 3' to the nucleic acid molecule encoding a light-labile, phytochrome A is disclosed. Methods for regulating a plant's canopy architecture and regulating a plant's seed yield, which involve transgenic plants or transgenic plant seeds including an isolated nucleic acid construct according to the present invention, are also disclosed.

17 Claims, 4 Drawing Sheets

FIGURE 1 A
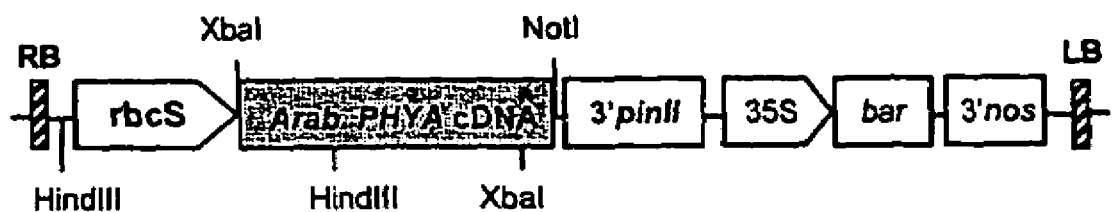
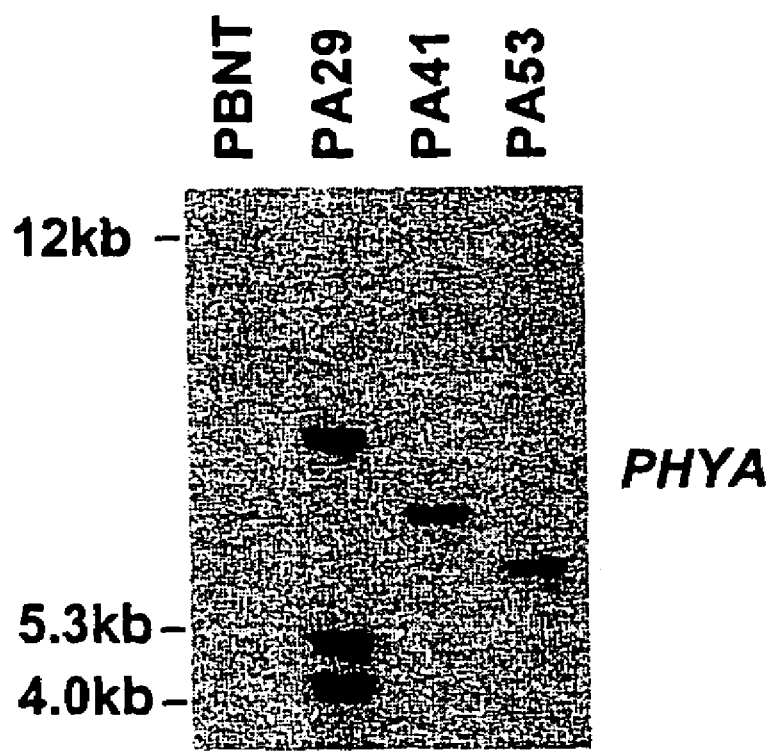
FIGURE 1 B

FIGURE 3 A
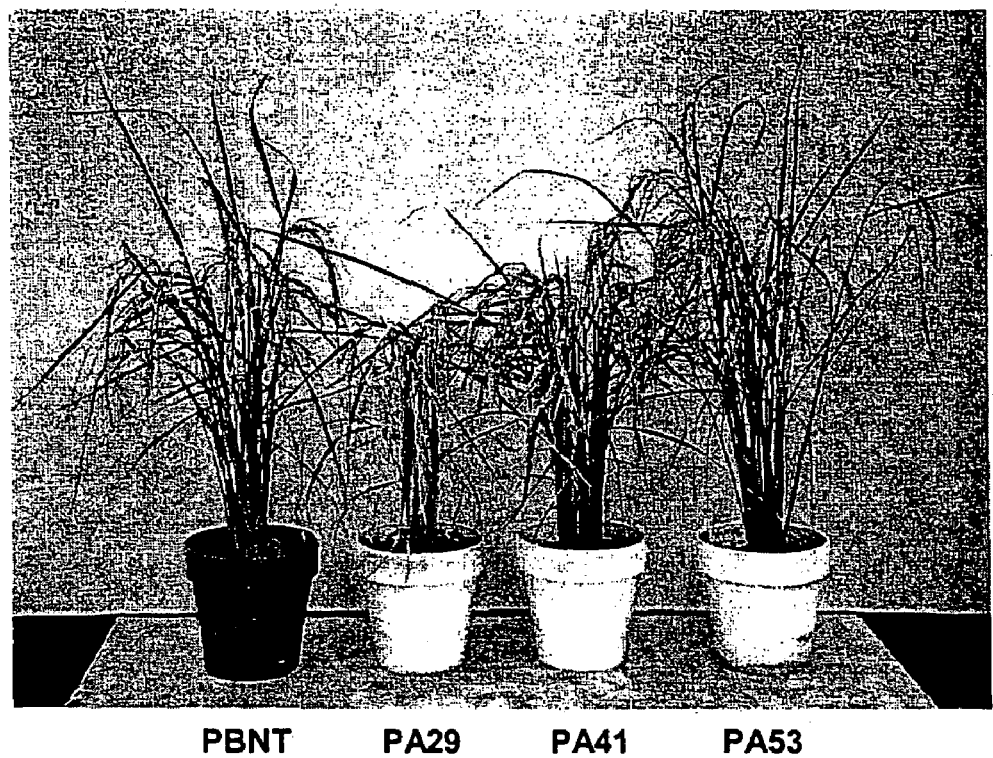
PBNT    PA29    PA41    PA53
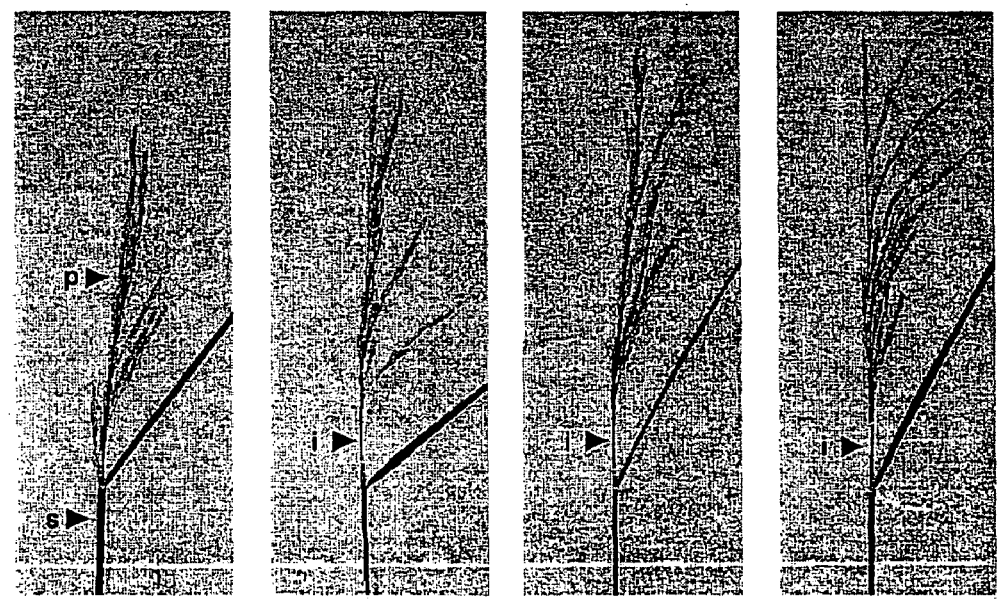
PBNT    PA29    PA41    PA53
FIGURE 3B

FIGURE 4A
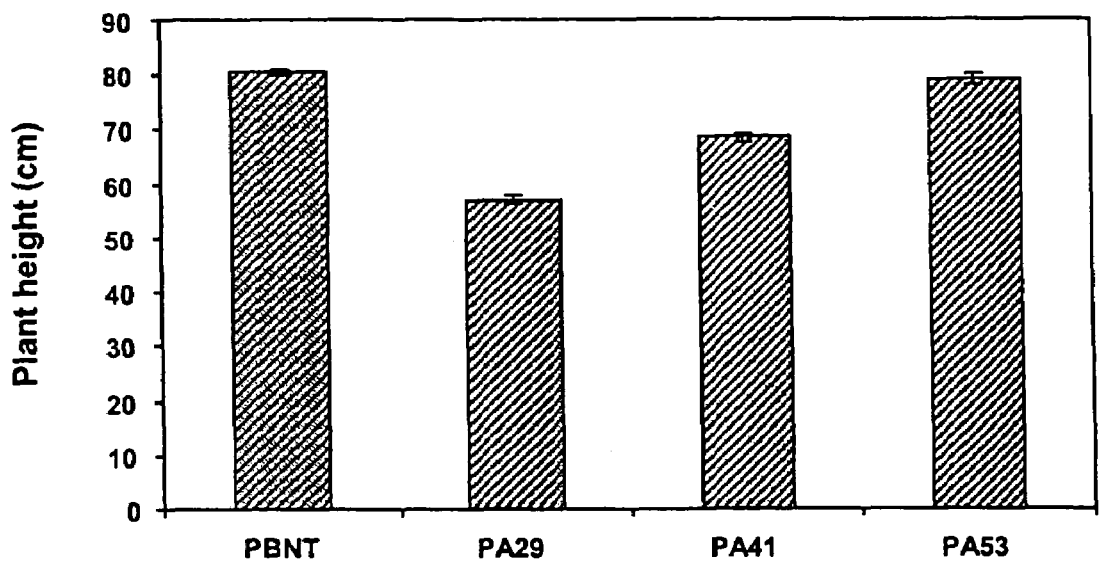
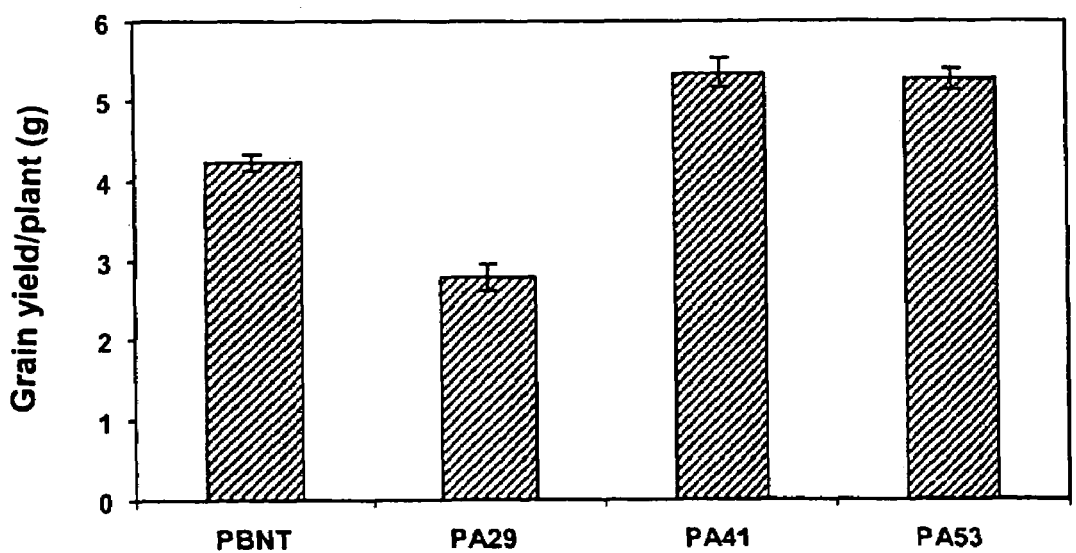
FIGURE 4B

TRANSGENIC EXPRESSION OF A PHYTOCHROME A GENE

This application claims the benefit of U.S. Provisional Patent Application Ser. No. 60/466,528, filed Apr. 29, 2003, which is hereby incorporated by reference in its entirety.

FIELD OF THE INVENTION

The present invention relates to the transgenic expression of a phytochrome A gene encoding a light-labile, phytochrome A protein.

BACKGROUND OF THE INVENTION

Crop productivity per unit area is a function of both available resources and how those resources are partitioned. The relative distribution of energies to different portions of the growing plant determines the proportion of useful biomass in the crop. This is referred to as the "harvest index". The pattern of resource allocation is plastic and can be regulated in response to changing environmental conditions, such as light and nutrient availability. However, adaptive competition strategies that have evolved through natural selection may be at odds with the agronomic performance of cultivated plants. The response exhibited by plants to competing vegetation has been termed "shade-avoidance", and is characterized by increased stem elongation, decreased leaf expansion, and precocious reproductive development. Smith, H., "Physiological and Ecological Function Within the Phytochrome Family," *Ann. Rev. Plant Physiol.—Plant Mol. Biol.* 46:289-315 (1995). The onset of shade avoidance is triggered by changes in the light environment caused by surrounding vegetation. Full sunlight contains equal fluxes of red light ("R") and far-red light ("FR"). Holmes et al., "The Function of Phytochrome in Plants Growing in the Natural Environment," *Nature* 254:512-514 (1975). However, when light filters through a crop canopy, the majority of R is either reflected or absorbed. Cumming, B., "The Dependence of Germination on Photoperiod, Light Quality and Temperature in *Chenopodium* sp.," *Can. J Bot.* 41:1211-1233 (1963). As a consequence, the ratio of R:FR falls from approximately 1 in incident sunlight, to approximately 0.2 at ground level. Holmes et al., "The Function of Phytochrome in Plants Growing in the Natural Environment," *Nature* 254:512-514 (1975). Plants use this change in R:FR ratio to monitor the proximity of local vegetation. Holmes et al., "The Function of Phytochrome in Plants Growing in the Natural Environment," *Nature* 254:512-514 (1975); Holmes et al., "The Function of Phytochrome in the Natural Environment IV, Light Quality and Plant Development," *Photochem. Photobiol.* 25:551-557 (1977). Although plants possess a number of photoreceptor systems that might mediate neighbor perception, genetic and physiological analyses have demonstrated that changes in R:FR ratio are primarily detected by members of the phytochrome family. Quail et al., "Phytochromes: Photosensory Perception and Signal Transduction," *Science* 268:675-680 (1995); Smith, H., "Phytochromes and Light Signal Perception by Plants—An Emerging Synthesis," *Nature* 407:585-591 (2000); Nagy et al., "Phytochromes Control Photomorphogenesis by Differentially Regulated, Interacting Signaling Pathways in Higher Plants," *Annu. Rev. Plant Biol.* 53:329-355 (2002).

The phytochromes are the best characterized family of photoreceptors, mediating many of the plant responses to changes in their light environment. Quail, P., "Phytochrome Photosensory Signaling Networks," *Nat. Rev. Mol. Cell Biol.* 3:85-93 (2002). In *Arabidopsis thaliana*, the phytochrome family consists of five genes: phytochrome A ("PHYA"), phytochrome B ("PHYB"), phytochrome C ("PHYC"), phytochrome D ("PHYD"), and phytochrome E ("PHYE"). Clack et al., "The Phytochrome Apoprotein Family in *Arabidopsis* is Encoded by Five Genes: The Sequences and Expression of PHYD and PHYE," *Plant Mol. Biol.* 25:413-427 (1994). In grasses, including rice, the family consists of only three members: PHYA, PHYB and PHYC. Dehesh et al., "PHYB is Evolutionarily Conserved and Constitutively Expressed in Rice Seedling Shoots," *Mol. Gen. Genet.* 225:305-313 (1991); Mathews et al., "The Phytochrome Gene Family in Grasses (*Poaceae*): A Phylogeny and Evidence That Grasses Have a Subset of the Loci Found in Dicot Angiosperms," *Mol. Biol. Evol.* 13:1141-1150 (1996). The basis of phytochrome action is the reversible photoconversion between a red light absorbing form ("$P_r$") and a far-red absorbing form ("$P_{fr}$"). Quail, P., "Phytochrome Photosensory Signaling Networks," *Nat. Rev. Mol. Cell Biol.* 3:85-93 (2002). Although this mechanism is common to all phytochromes, genetic analyses in *Arabidopsis* have shown that PHYA and PHYB have both distinct and overlapping roles during plant development. Whitelam et al., "Phytochrome A Null Mutants of *Arabidopsis* Display a Wild-type Phenotype in White Light," *Plant Cell* 5:757-768 (1993); Nagatani et al., "Isolation and Initial Characterization of *Arabidopsis* Mutants that are Deficient in Phytochrome A," *Plant Physiol.* 102:269-277 (1993).

Functional divergence between PHYA and PHYB is due, in part, to differences in $P_{fr}$ stability. Quail, P., "Phytochrome Photosensory Signaling Networks," *Nat. Rev. Mol. Cell Biol.* 3:85-93 (2002). PHYA is rapidly degraded following conversion of $P_r$ to $P_{fr}$, and it is most abundant prior to de-etiolation. Clough et al., "Phytochrome Degradation," *Plant Cell Environ.* 20:713-721 (1997). In contrast, PHYB is relatively light stable in both $P_r$ and $P_{fr}$ forms, and accumulates as the principal phytochrome in mature plants. Wagner et al., "Overexpression of Phytochrome B Induces a Short Hypocotyl Phenotype in Transgenic *Arabidopsis*," *Plant Cell* 3:1275-1288 (1991). PHYB mutants of *Arabidopsis* show a weak response to reductions in the R:FR ratio, and PHYB has been assigned a major role in the induction of the shade avoidance response. Whitelam et al., "Retention of Phytochrome-mediated Shade Avoidance Responses in Phytochrome-deficient Mutants of *Arabidopsis*, Cucumber, and Tomato," *J. Plant Physiol.* 139:119-125 (1991).

In view of the light-labile nature of PHYA, one of the more surprising results of genetic analyses has been the demonstration that PHYA is required for the normal development of light-grown plants. Johnson et al., "Photoresponses of Light-grown PHYA Mutants of *Arabidopsis*," *Plant. Physiol.* 105:141-149 (1994). Interestingly, PHYA plays a role in the regulation of plant architecture that appears to be antagonistic to that of PHYB. In a characterization of seedling growth, PHYA mutants of *Arabidopsis* displayed an exaggerated response to a reduction in the R:FR ratio, while transgenic tobacco plants expressing high levels of an oat PHYA displayed reduced sensitivity to changes in the R:FR ratio. Casal, J., "Phytochrome A Enhances the Promotion of Hypocotyl Growth Caused by Reductions in Levels of Phytochrome B in its Far-red-light-absorbing Form in Light-grown *Arabidopsis thaliana*," *Plant Physiol.* 110:965-973 (1996). In contrast, PHYA mutants of *japonica* rice (Nipponbare) did not show noticeable morphological changes in mature rice plants even though the expression pattern of chlorophyll a/b-binding proteins ("CAB") and small subunit of the Rubisco ("RbcS") was slightly altered. Takano et al., "Isolation and Characterization of Rice Phytochrome A Mutants," *Plant Cell* 13:521-534 (2001). Similarly, overexpression of rice PHYA partially complemented PHYB deficiency in *Arabidopsis*, but did not restore responses to low R:FR ratio. Halliday et al., "Overexpression of Rice Phytochrome A Partially Complements Phytochrome B Deficiency in *Arabidopsis*," *Planta* 207:401-409 (1999). Thus, precise roles for PHYA and PHYB in regulating mature plant development have been difficult to ascertain.

In recent years, shade avoidance has become a target of genetic modification of plants with the expectation that a reduction in the response may have positive effects upon yield. Based upon the characterization of light-signaling in *Arabidopsis*, these attempts have aimed to use the transgenic over-expression of PHYA to inhibit the action of PHYB. Clough et al., "Expression of a Functional Oat Phytochrome A in Transgenic Rice." *Plant Physiol.* 109:1039-1045 (1995); Robson et al., "Genetic Engineering of Harvest Index in Tobacco Through Overexpression of a Phytochrome Gene," *Nat. Biotechnol.* 14:995-998 (1996). Clough et al. successfully expressed an oat PHYA in rice under the control of the cauliflower mosaic virus (CaMV) 35S promoter, and detected a four-fold increase in total phytochrome activity in light-grown transgenic lines. However, under standard growth conditions, the phenotype of mature transgenic rice plants was indistinguishable from that of non-transgenic plants. Clough et al. concluded that a larger increase in the level of PHYA would be required to significantly alter the phenotype of the transgenic rice or that the *japonica* rice (Gulfinont) used in their study may be insensitive to increased PHYA levels.

Rice is the staple food for more than half of the world's population and therefore, stands as the world's most agronomically important crop. *Indica* rice varieties, including aromatic rices, represent 80% of rice grown worldwide. Aromatic rice varieties, including Basmati rice, are characterized by exquisite aroma and grain quality. Rani et al., "Current Status and Future Prospects for Improvement of Aromatic Rices in India," in Chaudhary et al., eds., *Specialty Rices of the World: Breeding Production and Marketing*, Science Publishers, Inc., Enfield, N.H., USA, pp. 49-78 (2000), and receive a premium price in global agricultural markets. Bhasin, V., "India and the Emerging Global Rice Market," in Singh et al., eds., *Aromatic Rices*, Science Publishers, Inc., Enfield, N.H., USA, pp. 257-276 (2000).

To date, however, it has been difficult to improve traditional Basmati cultivars into high yielding "elite" Basmati evolved lines by conventional rice breeding. This is mainly due to the complex nature of quality traits and the association of undesirable traits of Basmati, such as its tall stature, low yield, weak-stem and droopy leaves, sensitivity to photoperiod, and poor response to fertilizer. Khush et al., "Developing Basmati Rices with High Yield Potential," in Chaudhary et al., eds., *Specialty Rices of the World: Breeding Production and Marketing*, Science Publishers, Inc., Enfield, N.H., USA, pp. 49-78 (2000).; Rani et al., "Current Status and Future Prospects for Improvement of Aromatic Rices in India," in Chaudhary et al., eds., *Specialty Rices of the World: Breeding Production and Marketing*, Science Publishers, Inc., Enfield, N.H., USA, pp. 49-78 (2000). Hence, the development of genetically engineered Basmati plants with improved agronomic characteristics presents a current challenge in crop biotechnology.

The present invention is directed to overcoming these and other deficiencies in the art.

SUMMARY OF THE INVENTION

One aspect of the present invention concerns an isolated nucleic acid construct which includes a nucleic acid molecule encoding a light-labile, phytochrome A; a light-inducible promoter which is 5' to the nucleic acid molecule encoding a light-labile, phytochrome A; and a terminator region which is 3' to the nucleic acid molecule encoding a light-labile, phytochrome A. Another aspect of the invention provides an expression system including such a nucleic acid construct.

Further aspects of the invention concern a cell, a transgenic plant, and a transgenic plant seed, which include a nucleic acid construct according to the present invention.

A further aspect of the invention concerns a method of regulating a plant's canopy architecture. The method involves providing a transgenic plant, or a transgenic plant seed, which includes a nucleic acid construct according to the present invention, and growing the transgenic plant, or a plant grown from the transgenic plant seed, under conditions effective to regulate the plant's canopy architecture.

Yet another aspect of the invention concerns a method of regulating a plant's seed yield. The method involves providing a transgenic plant, or a transgenic plant seed, which includes a nucleic acid construct according to the present invention, and growing the transgenic plant, or a plant grown from the transgenic plant seed, under conditions effective to regulate the plant's seed yield.

The principles of the invention increase accumulation of a heterologous PHYA into a plant, such as, for example, a Basmati rice plant, to minimize or overcome the plant's shade-avoidance syndrome, and rationally alter its architecture and enhance its grain yield, without affecting its desirable quality traits. In accordance with one embodiment of the invention, the elite *indica* rice, Pusa Basmati-1 ("PBNT") was transformed with the *Arabidopsis* PHYA under the control of a light-regulated, tissue-specific, rice RbcS promoter, resulting in a large number of independent transgenic lines. Results from the fifth generation (generation "$T_4$") homozygous transgenic lines showed high levels of PHYA accumulation in the leaves of light-grown plants, and an increase in grain yield compared to nontransgenic plants. These results demonstrate the utility of the disclosed transgenic approach in developing new Basmati rice cultivars with increased grain yield.

BRIEF DESCRIPTION OF THE DRAWINGS

FIG. 1A is a schematic representation of an exemplary expression vector used for rice transformation in accordance with the present invention. T-DNA regions of the introduced plasmid pSBR 3.7 consist of the rice RbcS promoter linked to the *Arabidopsis* phytochrome A cDNA ("Arab PHYA cDNA"), the 3' region of the potato proteinase inhibitor II gene ("3' pinII"), and the bar gene expression cassette containing 35S promoter ("35S")/bar coding region ("bar")/3' region of the nopaline synthase gene ("3' nos"). "RB" and "LB" depict the right- and left-hand T-DNA border. Important restriction enzyme sites and the DNA probe fragment are also indicated.

FIG. 1B provides results of a Southern blot hybridization analysis. Genomic DNA from a non-transgenic control plant ("PBNT") and three independent lines transgenic plants ("PA29", "PA41", and "PA53") were digested with HindIII, and the blots were hybridized with a probe of 2.24 kb HindIII/XbaI fragment of PHYA coding region as shown in FIG. 1A. DNA molecular size markers (kb) are indicated.

FIGS. 3A and 3B show phenotypic differences between a non-transgenic plant ("PBNT") and plants overexpressing PHYA ("PA29", "PA41", and "PA53"). FIG. 3A illustrates representative mature rice plants of the non-transgenic line and three $T_4$-generation homozygous transgenic lines grown for about 20 weeks in the greenhouse. FIG. 3B illustrates a panicle of each of the four representative rice lines, showing the differences in the exsertion of the panicle and of the grain number per panicle.

FIGS. 4A and 4B are graphic representations of comparative agronomic performance of the non-transgenic control line ("PBNT") and the $T_4$-generation homozygous transgenic lines ("PA29", "PA41", and "PA53"). FIG. 4A compares plant height (cm), and FIG. 4B compares grain yield per plant (g). Values are the mean±SD (n=65).

DETAILED DESCRIPTION OF THE INVENTION

Figure 2:
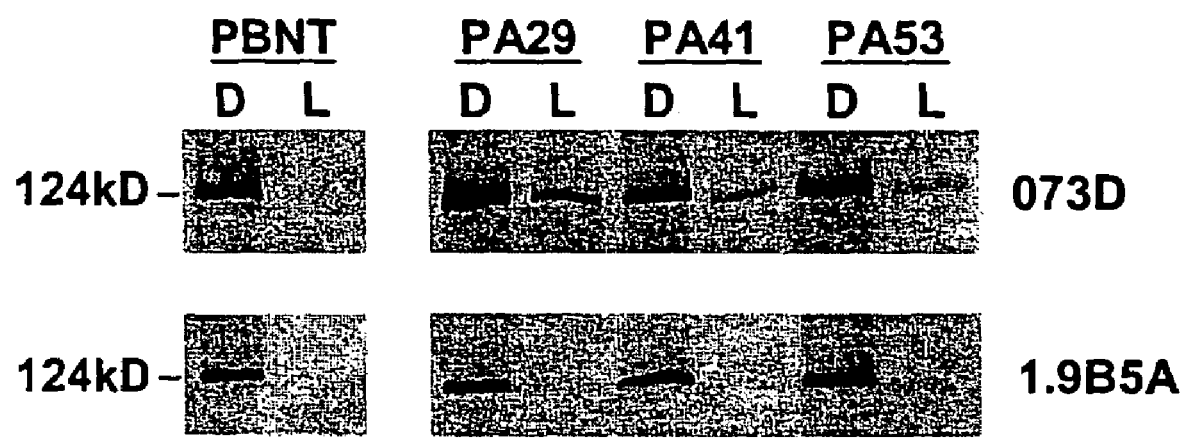
FIG. 2 provides immunoblot results for expression of *Arabidopsis* PHYA in transgenic rice. Total protein was extracted from etiolated ("D") and light-grown ("L"), non-transgenic ("PBNT") and transgenic ("PA29", "PA41", and "PA53") seedlings and analyzed by immunoblot. Blots were challenged either with an antibody that reacts with both rice and *Arabidopsis* PHYA ("O73D"), or with rice PHYA alone ("1.9B5A").

The present invention relates to a nucleic acid construct which includes a nucleic acid molecule encoding a light-labile, phytochrome A ("PHYA"); a light-inducible promoter which is 5' to the nucleic acid molecule encoding a light-labile, phytochrome A; and a terminator region which is 3' to the nucleic acid molecule encoding a light-labile, phytochrome A.

The light-labile, phyto chrome A may be from any number of species. The light-labile, phytochrome A may, for example, be obtained from *Arabidopsis thaliana* (NCBI GenBank Accession No. CAA35221, GI:16421), *Armoracia rusticana* (NCBI GenBank Accession No. BAA99408, GI:9049364), *Lycopersicon esculentum* (NCBI GenBank Accession No. CAA05086, GI:3492795), *Cucurbita pepo var. melopepo* (NCBI GenBank Accession No. FKPUZ, GI: 65877), *Pisum sativum* (NCBI GenBank Accession No. S06856, GI: 8193), *Nicotiana tabacum* (NCBI GenBank Accession No. CAA47284, GI:297478), *Populus tremula x Populus tremuloides* (NCBI GenBank Accession No. CAA04679, GI:2664190), *Lathyrus sativus* (NCBI GenBank Accession No. AAB47994, GI:1848273), *Solanum tuberosum* (NCBI GenBank Accession No. P30733, GI:464383), *Glycine max* (NCBI GenBank Accession No. AAA33957, GI:515749), *Stellaria longipes* (NCBI GenBank Accession No. AAQ11871, GI:33333476), *Petroselinum crispum* (NCBI GenBank Accession No. CAA53165, GI:556667), *Sorghum arundinaceum* (NCBI GenBank Accession No. AAR30893, GI:39777247), *Sorghum bicolor* (NCBI GenBank Accession No. AAR30887, GI:39777235), *Oryza sativa* (indica cultivar-group) (NCBI GenBank Accession No. GAA32375, GI:20288), *Sorghum propinquum* (NCBI GenBank Accession No. AAR30899, GI:39777259), *Oryza sativa* (japonica cultivar-group) (NCBI GenBank Accession No. AAM47309, GI:21321786), *Zea mays* (NCBI GenBank Accession No. JQ0382, GI:82715), *Avena sativa* (NCBI GenBank Accession No. A29631, GI:82338), *Picea abies* (NCBI GenBank Accession No. AAB03339, GI:1399958), *Marchantia paleacea var. diptera* (NCBI GenBank Accession No. BAB39687, GI:13429830), *Physcomitrella patens* (NCBI GenBank Accession No. AAM94952, GI:25986843), *Adiantum capillus-veneris* (NCBI GenBank Accession No. BAA33775, GI:3724346), *Selaginella martensii* (NCBI GenBank Accession No. CAA43698, GI:22603), *Ceratodon purpureus* (NCBI GenBank Accession No. AAB67863, GI:1314837), *Triticum aestivum* (NCBI GenBank Accession No. CAC82798, GI: 18076430), *Pinus sylvestris* (NCBI GenBank Accession No. CAA65510, GI:1237084), *Mesotaenium caldariorum* (NCBI GenBank Accession No. AAC49128, GI:1125699), *Nicotiana plumbaginifolia* (NCBI GenBank Accession No. CAA74992, GI:2370331), *Populus balsamifera subsp. trichocarpa* (NCBI GenBank Accession No. AAG25725, GI:10954091), *Mougeotia scalanis* (NCBI GenBank Accession No. CAA64796, GI:1419681), *Sorghum x drummondii* (NCBI GenBank Accession No. AAR30915, GI:39777291), *Oryza sativa* (NCBI GenBank Accession No. S14065, GI:100695), *Ipomoea nil* (NCBI GenBank Accession No. AAA84970, GI:1145714), *Psilotum nudum* (NCBI GenBank Accession No. CAA52883, GI:400480), *Hordeum vulgare* (NCBI GenBank Accession No. AAK97634, GI:15425967), *Houttuynia cordata* (NCBI GenBank Accession No. AAK20969, GI:13383412), *Asparagus falcatus* (NCBI GenBank Accession No. AAK20957, GI:13383388), *Tetracentron sinense* (NCBI GenBank Accession No. AAK20991, GI:13383456), *Pachysandra Americana* (NCBI GenBank Accession No. AAK20977, GI:13383428), *Heuchera Canadensis* (NCBI GenBank Accession No. AAK20967, GI:13383408), *Xanthorhiza simplicissima* (NCBI GenBank Accession No. AAK20993, GI:13383460), *Coptis trifolia* (NCBI GenBank Accession No. AAK20961, GI:1338396), *Akebia quinata* (NCBI GenBank Accession No. AAK20953, GI:13383380), *Lardizabala biternata* (NCBI GenBank Accession No. AAK20973, GI:13383420), *Sarcandra glabra* (NCBI GenBank Accession No. AAK20984, GI:13383442), *Hedyosmum sp. SM-2000* (NCBI GenBank Accession No. AAK20965, GI:13383404), *Aristolochia grandflora* (NCBI GenBank Accession No. AAK20955, GI:13383384), *Pseudowintera axillaris* (NCBI GenBank Accession No. AAK20980, GI:13383434), *Pteridophyllum racemogsum* (NCBI GenBank Accession No. AAK20982, GI:13383438), *Tacca chantieri* (NCBI GenBank Accession No. AAK20990, GI:13383454), *Ceratophyllum demersum* (NCBI GenBank Accession No. AAK20959, GI:13383392), *Hypecoum imberbe* (NCBI GenBank Accession No. AAK20970, GI:13383414), *Idiospermum australiense* (NCBI GenBank Accession No. AAF26335, GI:6715235), *Quiina pteridophylla* (NCBI GenBank Accession No. AAR30494, GI:39753893), *Pleea tenuifolia* (NCBI GenBank Accession No. AAK20979, GI:13383432), *Nelumbo nucifera* (NCBI GenBank Accession No. AAF26342, GI:6715242), *Degeneria vitiensis* (NCBI GenBank Accession No. AAF26324, GI:6715224), *Trochodendron aralioides* (NCBI GenBank Accession No. AAF26354, GI:6715254), *Aquilegia sp. SM-1999* (NCBI GenBank Accession No. AAF26312, GI:6715212), *Saururus cernuus* (NCBI GenBank Accession No. AAF26352, GI:6715252), *Lilium superbum* (NCBI GenBank Accession No. AAK20975, GI:13383424), *Saruma henryi* (NCBI GenBank Accession No. AAF26350, GI:6715250), *Smilax rotundifolia* (NCBI GenBank Accession No. AAK20986, GI:13383446), *Calycanthus floridus* (NCBI GenBank Accession No. AAF26318, GI:6715218), *Spathiphyllum clevelandii* (NCBI GenBank Accession No. AAK20988, GI:13383450), *Eupomatia laurina* (NCBI GenBank Accession No. AAF26328, GI:6715228), *Sagittaria sp. Mathews*383 (NCBI GenBank Accession No. AAF26348, GI:6715248), *Acorus gramineus* (NCBI GenBank Accession No. AAF26306, GI:6715206), *Hernandia lychnifera* (NCBI GenBank Accession No. AAF26332, GI:6715232), *Nymphaea odorata* (NCBI GenBank Accession No. AAF26344, GI:6715244), *Piper nigrum* (NCBI GenBank Accession No. AAF26346, GI:6715246), *Chioranthus spicatus* (NCBI GenBank Accession No. AAF26322, GI:6715222), *Annona* sp. *SM*-1999 (NCBI GenBank Accession No. AAF26310, GI:6715210), *Magnolia x soulangeana* (NCBI GenBank Accession No. AAF26340, GI:6715240), *Lactoris fernandeziana* (NCBI GenBank Accession No. AAF26337, GI:6715237), *Brasenia schreberi* (NCBI GenBank Accession No. AAF26316, GI:6715216), *Amborella trichopoda* (NCBI GenBank Accession No. AAF26308, GI:6715208), *Drimys winteri* (NCBI GenBank Accession No. AAF26326, GI:6715226), *Illicium oligandrum* (NCBI GenBank Accession No. AAK20972, GI:13383418), *Dioscorea elephantipes* (NCBI GenBank Accession No. AAK20964, GI:13383402), *Dissiliaria muelleri* (NCBI GenBank Accession No. AAR30464, GI:39753833), *Maytenus arbutifolia* (NCBI GenBank Accession No. AAR30480, GI:39753865), *Leonia glycycarpa* (NCBI GenBank Accession No. AAR30479, GI:39753863), *Peridiscus lucidus* (NCBI GenBank Accession No. AAR30489, GI:39753883), *Austrobuxus megacarpus* (NCBI GenBank Accession No. AAR30453, GI:39753811), *Dichapetalum macrocarpum* (NCBI GenBank Accession No. AAR30462, GI:39753829), *Acmanthera latifolia* (NCBI GenBank Accession No. AAM34150, GI:21069983), *Coleostachys genipifolia* (NCBI GenBank Accession No. AAM34149, GI:21069981), *Elaeodendron orientale* (NGBI GenBank Accession No. AAR30467, GI:39753839), *Androstachys johnsonii* (NCBI GenBank Accession No. AAM34144, GI:21069971), *Tristellateia madagascariensis* (NCBI GenBank Accession No. AAM34141, GI:21069965), *Balanops vieillardii* (NCBI GenBank Accession No. AAR30454, GI:39753813), *Petalostigma pubescens* (NCBI GenBank Accession No. AAR30490, GI:39753885), *Tristellateia Africana* (NCBI GenBank Accession No. AAM34170, GI:21070023), *Nymphaea alba* (NCBI GenBank Accession No. AAF26345, GI:6715245), *Dovyalis rhamnoides* (NCBI GenBank Accession No. AAR30465, GI:39753835), *Atuna racemosa* (NCBI GenBank Accession No. AAR30452, GI:39753809), *Spachea correae* (NCBI GenBank Accession No. AAM34197, GI:21070077), *Hirtella bicornis* (NCBI GenBank Accession No. AAR30473, GI:39753851), *Maytenus senegalensis* (NCBI GenBank Accession No. AAR30481, GI:39753867), *Canella winterana* (NCBI GenBank Accession No. AAF26321, GI:6715221), *Glandonia macrocarpa* (NCBI GenBank Accession No. AAM34195, GI:21070073), *Acridocarpus macrocalyx* (NCBI GenBank Accession No. AAM34154, GI:21069991), *Triopterys rigida* (NCBI GenBank Accession No. AAM34156, GI:21069995), *Ptilochaeta nudipes* (NCBI GenBank Accession No. AAM34190, GI:21070063), *Byrsonima crassifolia* (NCBI GenBank Accession No. AAM34148, GI:21069979), *Lophopterys floribunda (NCBI GenBank Accession No. AAM*34201, GI:21070085), *Diacidia ferruginea* (NCBI GenBank Accession No. AAM34126, GI:21069935), *Micrantheum hexandrum* (NCBI GenBank Accession No. AAR30483, GI:39753871), *Dillenia philippinensis* (NCBI GenBank Accession No. AAR30463, GI:39753831), and *Thryallis longifolia* (NCBI GenBank Accession No. AAM34173, GI:21070029). Sequence information for such phytochrome A is known in the art according to the National Center for Biotechnology Information ("NCBI") GenBank Accession No. and GenInfo Identifier ("GI").

Preferably, the light-labile, phytochrome A is from a dicot, such as, for example, *Arabidopsis*. The protein and DNA sequence of the *Arabidopsis* PHYA gene is known in the art, (NCBI GenBank Accession No. CAA35221, GI:16421).

Light-inducible promoters include, for example, a Rubisco promoter, or a chlorophyll a/b-binding protein promoter. Preferably, the light-inducible promoter is a RbcS promoter.

The invention further relates to an expression system involving a nucleic acid construct according to the present invention. Preferably, the nucleic acid construct is in proper sense orientation.

A nucleic acid construct according to the present invention may, for example, be incorporated into a host cell. Preferably, the host cell is a bacterial cell, or a plant cell.

A nucleic acid construct according to the present invention may, for example, be incorporated into a transgenic plant, or a transgenic plant seed. The transgenic plant, or a plant grown from the transgenic plant seed may be a monocot. Monocots, include, but are not limited to, for example, rice, wheat, barley, rye, corn, onion, garlic, and sugarcane. The transgenic plant, or a plant grown from the transgenic plant seed may, for example, be a rice plant. The rice plant may, for example, be of the *indica* or *japonica* variety. The rice plant may, for example, be of an aromatic variety. The rice plant may, for example, be Basmati rice.

The present invention also provides a method of regulating a plant's canopy architecture. The method involves providing a transgenic plant, or a transgenic plant seed, which has been transformed with a nucleic acid construct in accordance with the present invention. The transgenic plant, or a plant grown from the transgenic plant seed, is grown under conditions effective to regulate the plant's canopy architecture.

Preferably, the transgenic plant, or the plant grown from the transgenic plant seed, is a grain-producing plant, and regulating the plant's canopy architecture involves a reduction in plant height, an increase in exsertion or thrusting out, of a panicle portion of the plant, and/or an increase in tillering or branching of the panicle portion of the plant, as compared to that of a non-transgenic plant of the same type. Preferably, regulating the grain-producing plant's canopy architecture involves an increase in the number of filled grains per plant.

A further aspect of the present invention provides a method of regulating a plant's seed yield. The method involves providing a transgenic plant, or a transgenic plant seed, which has been transformed with a nucleic acid construct in accordance with the present invention. The transgenic plant, or a plant grown from the transgenic plant seed, is grown under conditions effective to regulate the plant's seed yield. Preferably, the plant's seed yield is increased.

The transgenic plant, or the plant grown from the transgenic plant seed, is preferably a grain-producing plant, and regulating the plant's seed yield involves increasing the grain yield of the plant through an increase in the number of filled grains per plant.

In accordance with the methods of the present invention, the transgenic plant, or the plant grown from a transgenic plant seed, is preferably a monocot, such as, for example, a rice plant. More preferably, the rice plant is of an indica rice variety, and in particular, an aromatic rice variety. Most preferably, the transgenic plant, or the plant grown from the transgenic plant seed, is a Basmati rice plant.

Another aspect of the invention is an expression system containing a nucleic acid construct in accordance with the present invention. The nucleic acid molecule encoding a light-labile, phytochrome A, may be inserted into any of the many available expression vectors and cell systems using reagents that are well known in the art.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC11, SV 40, pBluescript II SK +/− or KS +/− (see "Stratagene Cloning Systems" Catalog (1993) from Stratagene, La Jolla, Calif., USA, which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof.

In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens*. Fraley, et al., "Expression of Bacterial Genes in Plant Cells," *Proc. Nat'l Acad. Sci.*, 80:4803-4807 (1983), which is hereby incorporated by reference in its entirety.

Further improvement of this technique led to the development of the binary vector system. Bevan, M., "Binary *Agrobacterium* Vectors for Plant Transformation," *Nucleic Acids Res.* 12:8711-8721 (1984), which is hereby incorporated by reference in its entirety. In this system, all the T-DNA sequences (including the borders) are removed from the pTI, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19. Frisch, et al., "Complete Sequence of the Binary Vector Bin19," *Plant Molec. Biol.* 27:405-409 (1995), which is hereby incorporated by reference in its entirety. Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eukaryotic cells grown in tissue culture.

In one aspect of the present invention, the nucleic acid molecule encoding a light-labile, phytochrome A, is incorporated into an appropriate vector in the sense direction, such that the open reading frame is properly oriented for the expression of the encoded protein under control of a promoter of choice.

Certain "control elements" or "regulatory sequences" are also incorporated into the vector-construct. Those non-translated regions of the vector, promoters, 5' and 3' untranslated regions-which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopaline synthase (NOS) gene promoter, from *Agrobacterium tumefaciens*, (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter. Schena et al., "A Steroid-Inducible Gene Expression System for Plant Cells," *Proc. Natl. Acad. Sci.* 88:10421-5 (1991), which is hereby incorporated by reference in its entirety. Expression of the phytochrome A gene is induced in the plants transformed with the phytochrome A gene when the transgenic plants are brought into contact with nanomolar concentrations of a glucocorticoid, or by contact with dexamethasone, a glucocorticoid analog. Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11: 605-612 (1997), and McNellis et al., "Glucocorticoid-Inducible Expression of a Bacterial Avirulence Gene in Transgenic *Arabidopsis* Induces Hypersensitive Cell Death,

*Plant J.* 14(2):247-57 (1998), which are hereby incorporated by reference in their entirety. In addition, inducible promoters include promoters that function in a tissue specific manner to regulate the gene of interest within selected tissues of the plant. Examples of such tissue specific promoters include seed, flower, or root specific promoters as are well known in the field. U.S. Pat. No. 5,750,385 to Shewmaker et al., which is hereby incorporated by reference in its entirety.

The nucleic acid construct of the present invention also includes an operable 3' terminator region, selected from among those which are capable of providing correct transcription termination and polyadenylation of mRNA for expression in the host cell of choice, operably linked to a DNA molecule which encodes for a protein of choice. A number of 3' terminator regions are known to be operable in plants. Exemplary 3' terminator regions include, without limitation, the nopaline synthase 3' regulatory region (Fraley, et al., "Expression of Bacterial Genes in Plant Cells," *Proc. Nat'l Acad. Sci. USA* 80:4803-4807 (1983), which is hereby incorporated by reference in its entirety) and the cauliflower mosaic virus 3' regulatory region. Odell, et al., "Identification of DNA Sequences Required for Activity of the Cauliflower Mosaic Virus 35S Promoter," *Nature* 313 (6005):810-812 (1985), which is hereby incorporated by reference in its entirety. Virtually any 3' terminator region known to be operable in plants would suffice for proper expression of the coding sequence of the nucleic acid construct of the present invention.

The vector of choice, promoter, and an appropriate 3' terminator region can be ligated together to produce the plasmid of the present invention using well known molecular cloning techniques as described in Sambrook et al., *Molecular Cloning: A Laboratory Manual*, Second Edition, Cold Spring Harbor Press, N.Y. (1989), and Ausubel, F. M. et al. (1989) *Current Protocols in Molecular Biology*, John Wiley & Sons, New York, N.Y., which are hereby incorporated by reference in their entirety.

Once the DNA construct of the present invention has been prepared, it is ready to be incorporated into a host cell. Recombinant molecules can be introduced into cells via transformation, particularly transduction, conjugation, mobilization, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell.

Accordingly, another aspect of the present invention relates to a method of making a recombinant cell. Basically, this method is carried out by transforming a plant cell with the nucleic acid construct of the present invention under conditions effective to yield transcription of the nucleic acid molecule in the plant cell. Preferably, the nucleic acid molecule of the present invention is stably inserted into the genome of the recombinant plant cell as a result of the transformation.

One approach to transforming plant cells with the nucleic acid molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford, et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression since the population of cells is very high (on the order of $10^6$). To deliver DNA inside protoplasts, several methodologies have been proposed, but the most common are electroporation (Fromm et al., "Expression of Genes Transferred Into Monocot and Dicot Plants by Electroporation," *Proc. Nati. Acad. Sci. USA* 82:5824-5828 (1985), which is hereby incorporated by reference in its entirety) and polyethylene glycol (PEG) mediated DNA uptake. Krens et al., "In Vitro Transformation of Plant Protoplasts with Ti-Plasmid DNA," *Nature* 296:72-74 (1982), which is hereby incorporated by reference in its entirety. During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, either minicells, cells, lysosomes, or other fusible lipid-surfaced bodies that contain the chimeric gene. Fraley, et al., *Proc. Natl. Acad. Sci. USA,* 79:1859-63 (1982), which is hereby incorporated by reference in its entirety.

Stable transformants are preferable for the methods of the present invention. An appropriate method of stably introducing the nucleic acid construct into plant cells is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants. In one embodiment of the present invention transformants are generated using the method of Frary et al, *Plant Cell Reports* 16: 235 (1996), which is hereby incorporated by reference in its entirety, to transform seedling explants.

Plant tissues suitable for transformation include, but are not limited to, floral buds, leaf tissue, root tissue, meristems, zygotic and somatic embryos, megaspores, and anthers.

After transformation, the transformed plant cells can be selected and regenerated. Preferably, transformed cells are first identified using a selection marker simultaneously introduced into the host cells along with the nucleic acid construct of the present invention. The most widely used reporter gene for gene fusion experiments has been uidA, a gene from *Escherichia coli* that encodes the β-glucuronidase protein, also known as GUS. Jefferson et al., "GUS Fusions: βGlucuronidase as a Sensitive and Versatile Gene Fusion Marker in Higher Plants," *EMBO Journal* 6:3901-3907 (1987), which is hereby incorporated by reference in its entirety. GUS is a 68.2 kd protein that acts as a tetramer in its native form. It does not require cofactors or special ionic conditions, although it can be inhibited by divalent cations like $Cu^{2+}$ or $Zn^{2+}$. GUS is active in the presence of thiol reducing agents like β-mercaptoethanol or dithiothreitol (DTT).

In order to evaluate GUS activity, several substrates are available. The most commonly used are 5 bromo-4 chloro-3 indolyl glucuronide (X-Gluc) and 4 methyl-umbelliferyl-glucuronide (MUG). The reaction with X-Gluc generates a blue color that is useful in histochemical detection of the gene activity. For quantification purposes, MUG is preferred, because the umbelliferyl radical emits fluorescence under UV stimulation, thus providing better sensitivity and easy measurement by fluorometry. Jefferson et al., "GUS Fusions: β Glucuronidase as a Sensitive and Versatile Gene Fusion Marker in Higher Plants," *EMBO Journal* 6:3901-3907 (1987), which is hereby incorporated by reference in its entirety.

Other suitable selection markers include, without limitation, markers encoding for antibiotic resistance, such as the nptII gene which confers kanamycin resistance (Fraley, et al., *Proc. Natl. Acad. Sci. USA*, 80:4803-4807 (1983), which is hereby incorporated by reference in its entirety) and the dhfr gene, which confers resistance to methotrexate. Bourouis et al., *EMBO Journal* 2:1099-1104 (1983), which is hereby incorporated by reference in its entirety. A number of antibiotic-resistance markers are known in the art and others are continually being identified. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. Means for regeneration vary from species to species of plants, but generally a suspension of transformed protoplasts or a petri plate containing transformed explants is first provided. Callus tissue is formed and shoots may be induced from callus and subsequently rooted. Alteratively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures*, Vol. 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference in their entirety.

It is known that practically all plants can be regenerated from cultured cells or tissues, including but not limited to, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

After the nucleic acid molecule of the present invention is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds are recovered from the transgenic plants. The seeds can then be planted in the soil and cultivated using conventional procedures to produce transgenic plants.

EXAMPLES

Example 1

Plasmid Construction

The binary plasmid, pSBR 3.7 containing a full-length *Arabidopsis* PHYA cDNA (Sharrock et al., "Novel Phytochrome Sequences in *Arabidopsis thaliana*: Structure, Evolution, and Differential Expression of a Plant Regulatory Photoreceptor Family," *Genes Dev.* 3:1745-1757 (1989), which is hereby incorporated by reference in its entirety) was constructed in the pSB11 vector (Komari et al., "Vectors Carrying Two Separate T-DNAs for Co-transformation of Higher Plants Mediated by *Agrobacterium tumefaciens* and Segregation of Transformants Free From Selection Markers," *Plant J.* 10-165-174 (1996), which is hereby incorporated by reference in its entirety) using standard cloning and plasmid manipulations procedures. The components of the plasmid within the T-DNA region, and the selected restriction enzyme sites are shown in FIG. 1A. The expression cassette in pSBR 3.7 consists of the 1.3 kb rice RbcS promoter (Kyozuka et al., "Light-regulated and Cell-specific Expression of Tomato RbcS-gusA and Rice RbcS-gusA Fusion Genes in Transgenic Rice," *Plant Physiol.* 102:991-1000 (1993), which is hereby incorporated by reference in its entirety) that is linked to the *Arabidopsis* PHYA coding region (3.7 kb), and the 3' region of the potato proteinase inhibitor II gene (3' pinII) non-coding sequence (1.0 kb). The selection cassette includes the cauliflower mosaic virus ("CaMV") 35S promoter (0.74 kb), phosphinothricin acetyl-transferase gene (bar, 0.59 kb), and the nopaline synthase gene 3' non-coding sequence (3'-nos, 0.28 kb). The plasmid pSBR 3.7 was mobilized into *Agrobacterium tumefaciens* strain LBA4404 harboring pSB1 (Komari et al., "Vectors Carrying Two Separate T-DNAs for Co-transformation of Higher Plants Mediated by *Agrobacterium tumefaciens* and Segregation of Transformants Free From Selection Markers," *Plant J.* 10-165-174 (1996), which is hereby incorporated by reference in its entirety) by triparental mating using the helper plasmid pRK2013. For co-cultivation, the bacteria were grown from a single colony in liquid AB medium containing 50 mg/liter spectinomycin at 30° C. for 3 days, and were suspended at a density of $3 \times 10^9$ cells/ml in AAM medium (Hiei et al., "Efficient Transformation of Rice (*Oryza sativa* L.) Mediated by *Agrobacterium* and Sequence Analysis of the Boundaries of the T-DNA," *Plant J.* 2:271-282 (1994), which is hereby incorporated by reference in its entirety) for rice transformation.

Example 2

Generation of Transgenic Rice Plants

Agrobacterium-mediated transformation of indica rice variety Pusa Basmati-1 ("PBNT") was carried out as described earlier. Garg et al., "Trehalose Accumulation in Rice Plants Confers High Tolerance Levels to Different Abiotic Stresses," *Proc. Natl. Acad. Sci. USA* 99:15898-15903 (2002), which is hereby incorporated by reference in its entirety. Briefly, scutella-derived embryogenic calli were used for co-cultivation with Agrobacterium tumefaciens strain LBA4404 harboring pSBR 3.7. Three days after co-cultivation, calli were selected on a callusing medium containing 6 mg/liter bialaphos and 250 mg/liter cefotaxime. Further, micro-calli that had proliferated on fresh selection medium (two selection cycles) were transferred to regeneration medium containing 4 mg/liter bialaphos. The regenerated plantlets were acclimatized hydroponically in Yoshida nutrient solution, transferred to pots and tested for Basta-herbicide resistance. Roy et al., "Arginine Decarboxylase Transgene Expression and Analysis of Environmental Stress Tolerance in Transgenic Rice," *Plant Sci.* 160:869-875 (2001), which is hereby incorporated by reference in its entirety. Primary transgenic plants were grown to maturity in a greenhouse and designated as the $T_0$-generation plants. The $T_0$ plants were continuously selfed through four generations to obtain homozygous $T_4$ transgenic seeds for phenotypic analysis.

Example 3

DNA-blot Hybridization Analysis

Leaves from a non-transgenic control ("PBNT") plant, and forty-three independent putative $T_0$ transformants that were transformed with the plasmid pSBR 3.7, were ground in liquid nitrogen using a mortar and pestle. Rice genomic DNA was isolated by the guanidine-detergent lysis method using $DNAzol^{ES}$ (Molecular Research Center, Inc., Cincinnati, Ohio, USA) following the manufacturer's instructions. Five micrograms of the genomic DNA was digested overnight with the HindIII restriction enzyme, fractionated through 0.8% agarose gel, alkali transferred onto Hybond N+nylon membrane (Amersham Pharmacia, Piscataway, N.J., USA) and hybridized with $\alpha$-$^{32}$P-labeled, 2.24 kb Arabidopsis PHYA coding region (HindIII and XbaI fragment) as the probe. DNA probe preparation, hybridization, and washing of the membrane were performed as described. Roy et al., "Arginine Decarboxylase Transgene Expression and Analysis of Environmental Stress Tolerance in Transgenic Rice," *Plant Sci.* 160:869-875 (2001), which is hereby incorporated by reference in its entirety. The $\alpha$-$^{32}$P-labeled membrane was exposed onto autoradiogram.

Example 4

Immunological Detection of Phytochrome

Seedlings ($T_4$-generation) were frozen in liquid nitrogen, ground to a fine powder and suspended in extraction buffer (2 ml g$^{-1}$) that consists of 37.5% (v/v) ethylene glycol, 75 mM Tris-HCl (pH 8.3), 7.5 mM Na$_2$EDTA, 15 mM NaS$_2$O$_5$, 0.11% (v/v) polyethylenimine, 1.5 mM phenylmethylsulfonyl fluoride. Davis et al., "The Heme-oxygenase Family Required for Phytochrome Chromophore Biosynthesis is Necessary for Proper Photomorphogenesis in Higher Plants," *Plant Physiol.* 126:656-669 (2001), which is hereby incorporated by reference in its entirety. The extract was clarified by centrifugation at 3000 g for 30 min. at 4° C., fractionated by SDS-PAGE (7.5% acrylamide gel) and transferred to nitrocellulose membrane (Schleicher and Schuell BioScience, Inc., Keene, N.H., USA). Each lane of the gel was loaded with 50 µg total protein from dark- or light-grown seedlings as determined using the Bio-Rad DC protein assay antibody (Bio-Rad Laboratories, Hercules, Calif., USA). The proteins were fractionated by SDS-PAGE and transferred to nitrocellulose membrane. Duplicate blots were challenged either with a monoclonal antibody O73D (1:500 dilution) that reacts with both Arabidopsis PHYA and rice PHYA, or with a monoclonal antibody 1.9B5A (1:1000 dilution) that reacts with rice PHYA alone. Proteins on filter were visualized after treatments with horseradish peroxidase conjugated goat-anti-mouse secondary antibody and the Bio-Rad Opti-4CN substrate kit (Bio-Rad Laboratories, Hercules, Calif., USA). Molecular masses (kD) were determined using pre-stained markers (SeeBlue® Plus 2, Invitrogen® Corporation, Carlsbad, Calif.).

Example 5

Phenotypic Analysis of Transgenic Rice Plants Grown in Greenhouses

Seeds of the non-transgenic line ("PBNT") and the $T_4$-generation homozygous transgenic lines ("PA29", "PA41", and "PA53") were sown and germinated in small pots containing sterilized topsoil, and three-weeks-old seedlings were then transplanted to bigger pots (20×20 cm, one plant per pot) in a contained greenhouse at Cornell University, Ithaca, N.Y., USA. Plants were grown under metal-halide white light with a photoperiod of 10 hr light/14 hr dark, 50-60% relative humidity, and 28° C. day/24° C. night temperature. All the plants were irrigated daily and fertilizer was periodically applied as necessary. The plants were grown to maturity and common agronomic traits (including, plant height, 1000-grain weight, and grain yield/plant) were evaluated. Plant height was measured from the inner rim of the pot (base of the stem) to the tip of the tallest panicle ("p"). The grain yield/plant and 1000-grain weight were measured after the seeds were dried at 37° C. for 10 days. Variation in plant height was investigated using general linear model ("GLM") analysis following the requirements of each test (Stell and Torries, CITATION (1980)) using Minitab® software (Minitab, Inc., State College, Pa., USA). Within line variation in yield was normally distributed allowing between-line variation to be investigated by GLM analysis. The normality of distributions was evaluated using the ANOVA and two-sample t-test. Data sets not showing a normal distribution were square root transformed to conform to the assumption of ANOVA analysis. A pooled estimate of variance was used for t-tests. The relationship between yield and other measured traits was examined by linear regression.

Example 6

Generation of Transgenic Rice Lines Expressing Arabidopsis Phytochrome A

In an attempt to antagonize the shade avoidance response, Basmati transgenic rice lines were generated expressing the Arabidopsis PHYA. Embryogenic calli were transformed with a plasmid (PSBR 3.7) containing the Arabidopsis PHYA coding region under the control of a light-regulated and tissue-specific RbcS promoter (FIG. 1A). The plasmid also contained the coding region of the phosphinothricin acetyltransferase (bar) gene under the control of constitutive CaMV 35S promoter to allow selection of transformants on the basis of resistance to the phosphinothricin-based herbicide Basta. From 120 calli co-cultivated with *Agrobacterium tumefaciens* containing pSBR 3.7, fifty-one plants were regenerated, of which forty-six were Basta resistant. Among the $T_0$-generation lines, 92% were fertile and set normal seeds. Detailed molecular and phenotypic characterization were conducted on several homozygous transgenic plants up to the $T_4$-generation, because gene silencing has been reported to occur in the $T_3$-generation even though $T_2$- and $T_1$-generation plants were not silenced. Iyer et al., "Transgene Silencing in Monocots," *Plant Mol. Biol.* 43:323-346 (2000), which is hereby incorporated by reference in its entirety.

Example 7

Southern Blot Analysis of Transgenic Lines

Southern blot analysis was used to confirm transgene integration and to determine transgene copy number. Genomic DNA was isolated from Basta-resistant transgenic plants and non-transgenic control plants and digested with HindIII for T-DNA junction fragment analysis (FIG. 1A). The resulting Southern blot was hybridized with a labeled 2.24 kb *Arabidopsis* PHYA fragment that was obtained by HindIII/XbaI digestion of pSBR 3.7 (FIG. 1A). The PHYA probe hybridized to one or more fragments of digested DNA from transgenic plants depending upon transgene copy number. The PHYA probe hybridized to DNA extracted from thirty-nine of forty-three Basta resistant plants analyzed. Of these, eight contained a single copy of the transgene, ten contained two copies, and ten contained three copies. The Southern analysis of three lines chosen for further study is shown in FIG. 1B. No hybridization was seen to DNA extracted from non-transgenic plants. The line PA29 contains three independently inserted copies of the transgene, whereas lines PA41 and PA53 each contain a single copy. Analyses of Basta resistance from twelve independent transgenic lines in the $T_1$-generation showed a segregation pattern of 3:1 for the Basta-herbicide resistance marker gene in eight rice lines that include PA41 and PA53.

Example 8

Immunodetection of Phytochrome A in Transgenic Rice Seedlings

Immunoblot analysis was used to confirm the accumulation of full length *Arabidopsis* PHYA in transgenic rice lines PA29, PA41, and PA53. Total leaf protein was extracted from etiolated and white-light grown seedlings, fractionated by SDS-PAGE and transferred to nitrocellulose membrane. Duplicate blots were challenged either with a monoclonal antibody that reacts with both *Arabidopsis* PHYA and rice PHYA ("O73D") or with a monoclonal antibody that reacts specifically with monocot PHYA ("1.9B5A"). The results were consistent with known patterns of PHYA accumulation, both O73D and 1.9B5A detected a protein of approximately 124 kD in etiolated non-transgenic seedlings, whereas this protein was absent in white-light grown plants. In transgenic plants, no ectopic accumulation of endogenous PHYA was detected in white-light grown plants (FIG. 2B). However, the accumulation of the *Arabidopsis* protein was detected in all transgenic lines examined (FIG. 2A). Total PHYA accumulation in etiolated transgenic seedlings was not dramatically different from that in non-transgenic plants. This result is consistent with the known activity of the RbcS promoter that drives expression in light grown leaf tissue. Kyozuka et al., "Light-regulated and Cell-specific Expression of Tomato RbcS-gusA and Rice RbcS-gusA Fusion Genes in Transgenic Rice," *Plant Physiol.* 102:991-1000 (1993), which is hereby incorporated by reference in its entirety.

Example 9

Architecture and Grain Yield of Transgenic Rice Plants Grown In Greenhouses

When grown under periodic white light in a greenhouse, transgenic rice plants expressing *Arabidopsis* PHYA were reduced in height and showed an increase in tillering (branching), resulting in a more bushy appearance than non-transgenic plants (FIG. 3A). In the extreme case of PA29, a line carrying three copies of the transgene and accumulating the highest levels of PHYA (as determined by immunoblot), dwarfing is apparent (FIG. 3A). As shown in FIG. 4A, the height differed significantly between lines (ANOVA, $F=161.48$, $p<0.001$). The lines PA29 and PA41 were significantly shorter than non-transgenic control plants (PA29: $t=15.9$, $p<0.001$; PA41: $t=8.10$, $p<0.001$). The line PA53 was not significantly different in height from controls ($t=1.132$, $p=0.2$). All three transgenic lines characterized exhibited a greater degree of panicle exsertion than non-transgenic control plants (FIG. 3B). In non-transgenic plants, basal portions of the panicle ("p") were partially enclosed by the flag leaf sheath ("s"). In contrast, in transgenic lines, the panicle and subtending internode ("i") were entirely exposed.

Grain yield was quantified on the basis of total grain weight per plant (FIG. 4B). Yield measures differed significantly between lines (ANOVA, $F=64.46$, $p<0.001$). Line PA29 was estimated to yield less than non-transgenic control plants ($t=5.6$, $p<0.001$), whereas lines PA41 and PA53 were both estimated to yield greater than non-transgenic plants (PA41: $t=4.4$, $p<0.001$; PA53: $t=4.0$, $p<0.001$). Compared to non-transgenic control plants, transgenic lines PA41 and PA53 gave increased yields of 27% and 25%, respectively. There was no significant difference between the yields of lines PA41 and PA53. Thousand-grain weight was measured and no significant difference found between transgenic and non-transgenic lines (e.g., $21.0\pm0.5$ for PBNT and $21.7\pm0.4$ for PA53). Therefore, the increased yield in lines PA41 and PA53 can be attributed to an increase in the number of filled grains per plant.

Transgenic Basmati rice plants grown to maturity under periodic white light in the greenhouse showed altered patterns of growth. Importantly, two of the lines characterized (lines PA41 and PA53) were found to produce a greater mass of grain per plant than non-transgenic control plants. These observations contrast with a previous study in which overexpression of PHYA in japonica rice (Gulfinont) did not result in morphological changes to mature plants. Clough et al., "Expression of a Functional Oat Phytochrome A in Transgenic Rice," *Plant Physiol.* 109:1039-1045 (1995), which is hereby incorporated by reference in its entirety.

Light-inducible promoters are able to respond to a wide spectrum of light through multiple photoreceptor system. Martinez-Hernandez et al., "Functional Properties and Regulatory Complexity of a Minimal RbcS Light-responsive Unit Activated by Phytochrome, Cryptochrome, and Plastid Signals," *Plant Physiol.* (2002), which is hereby incorporated by reference in its entirety. Deletion and mutagenesis analysis of the promoter region of photosynthesis-associated nuclear genes, particularly those encoding the RbcS and CAB, have led to the identification of a number of cis-acting elements involved in the control of transcription by light. Kyozuka et al., "Light-regulated and Cell-specific Expression of Tomato RbcS-gusA and Rice RbcS-gusA Fusion Genes in Transgenic Rice," *Plant Physiol.* 102:991-1000 (1993); Martinez-Hernandez et al., "Functional Properties and Regulatory Complexity of a Minimal RbcS Light-responsive Unit Activated by Phytochrome, Cryptochrome, and Plastid Signals," *Plant Physiol.* (2002), which are hereby incorporated by reference in their entirety. However, how these cis-acting light-responsive elements within the RbcS promoter activate different signal transduction pathways and target different transcription factors and/or a given gene, is not completely understood. Gilmartin et al., "Localization of a Phytochrome-responsive Element Within the Upstream Region of Pea RbcS-3A," *Mol. Cell Biol.* 10:5565-5568 (1990); Kyozuka et al., "Light-regulated and Cell-specific Expression of Tomato RbcS-gusA and Rice RbcS-gusA Fusion Genes in Transgenic Rice," *Plant Physiol.* 102:991-1000 (1993), which are hereby incorporated by reference in their entirety.

Photoactive PHYA holophytochrome consists of the PHYA apoprotein covalently attached to a linear tetrapyrrole (bilin) chromophore. Terry, M., "Phytochrome Chromophore-deficient Mutants," *Plant Cell Environ.* 20:740-745 (1997), which is hereby incorporated by reference in its entirety. The evolutionary conservation of the activities required for chromophore synthesis and holophytochrome assembly has been demonstrated between a number of species (Boylan et al., "Oat Phytochrome is Biologically Active in Transgenic Tomatoes," *Plant Cell* 1:765-773 (1989); Boylan et al., "Phytochrome A Overexpression Inhibits Hypocotyl Elongation in Transgenic *Arabidopsis*," *Proc. Natl. Acad. Sci. USA* 88:10806-10810 (1991); Clough et al., "Expression of a Functional Oat Phytochrome A in Transgenic Rice," *Plant Physiol.* 109:1039-1045 (1995); Kay et al., "Rice Phytochrome is Biologically Active in Transgenic Tobacco," *Plant Cell* 1:775-782 (1989), which are hereby incorporated by reference in their entirety) and it is predicted that *Arabidopsis* PHYA will be correctly processed in rice to form active holoprotein. Such studies have also suggested that heterologous PHYA proteins retain the capacity to interact with downstream components of the light signal transduction chain. However, it should be noted that previous reports have examined the effects of overexpressing a monocot PHYA in both monocots and dicots, and no quantitative measurements of the activity of *Arabidopsis* PHYA in a monocot have been made. In the absence of such data, the phenotypic consequences of transgene introduction offer the strongest evidence that *Arabidopsis* phytochrome is biologically active in the rice lines PA29, PA41 and PA53.

When grown to maturity in the greenhouse under periodic white light, lines PA29 and PA41 exhibited dwarfism following an inhibition of elongation growth. Previously characterized PHYA overexpressing lines in a number of species show a similar phenotype. The expression of the oat PHYA in tomato (*Lycopersicon esculentum* cv VF36) resulted in dwarfing and an increase in pigmentation of both leaves and fruits. Boylan et al., "Oat Phytochrome is Biologically Active in Transgenic Tomatoes," *Plant Cell* 1:765-773 (1989), which is hereby incorporated by reference in its entirety. Similarly, tobacco plants (*Nicotiana tabacum* cv Xanthi) expressing the rice PHYA showed shorter stems and dark green leaves. Nagatani et al., "Rice Type I Phytochrome Regulates Hypocotyl Elongation in Transgenic Tobacco Seedlings," *Proc. Natl. Acad. Sci ISA* 88:5207-5211 (1991), which is hereby incorporated by reference in its entirety. However, a comparable study in which rice PHYA was expressed in the tobacco variety SRi, found no morphological phenotype associated with transgene expression. Kay et al., "Rice Phytochrome is Biologically Active in Transgenic Tobacco," *Plant Cell* 1:775-782 (1989), which is hereby incorporated by reference in its entirety. These data suggest that genetic modifiers may dramatically influence the phytochrome response pathway. Such background differences may account for the differing phenotypes of the PHYA overexpressing japonica rice line characterized by Clough et al. ("Expression of a Functional Oat Phytochrome A in Transgenic Rice," *Plant Physiol.* 109:1039-1045 (1995), which is hereby incorporated by reference in its entirety) and the indica rice lines PA29, PA41 and PA53.

Detailed studies of the mature plant phenotype of PHYA-overexpressing plants has demonstrated the importance of environmental effects and implicated a disruption of the shade avoidance response in conditioning altered plant architecture. The degree of dwarfing exhibited by tobacco plants (*Nicotiana tabacum* cv Xanthi) expressing oat PHYA was found to be dependent upon planting density. Robson et al., "Genetic Engineering of Harvest Index in Tobacco Through Overexpression of a Phytochrome Gene," *Nat. Biotechnol.* 14:995-998 (1996), which is hereby incorporated by reference in its entirety. As plants were grown at higher densities, the height of transgenic plants was reduced in a phenomenon termed "proximity-conditional dwarfing". Coupled with the reduction in stem elongation was an allocation of growth assimilates to leaf growth, and a consequent increase in harvest index. The reallocation of resources in transgenic plants was termed "reverse shade avoidance" and interpreted as the result of an antagonism of PHYA and PHYB. The partial dwarfing of rice lines PA29 and PA41 under standard planting densities is consistent with a reverse shade avoidance response.

The expression of *Arabidopsis* PHYA in a commercially important Basmati rice variety has allowed the selection of lines showing appreciable gains in total grain yield under greenhouse growth conditions. It remains to be seen whether these gains are maintained in field trials and under which field conditions transgenic lines have a performance advantage. Nevertheless, the analysis of these lines carrying both single and multiple copies of the PHYA trans gene has already demonstrated that variations in PHYA expression can have dramatic effects on yield. It is believed that the further characterization of transgenic rice lines PA29, PA41, and PA53 will lead to an increased understanding of the role of light signaling in plant development and aid in the improvement of crop productivity.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A transgenic monocot plant comprising a nucleic acid construct comprising:

a nucleic acid molecule encoding a light-labile, phytochrome A from *Arabidopsis;* a light-inducible promoter which is 5' to the nucleic acid molecule encoding a light-labile, phytochrome A; and a terminator region which is 3' to the nucleic acid molecule encoding a light-labile phytochrome A, wherein the transgenic monocot plant exhibits increased seed yield, as compared to a non-transgenic monocot plant of the same type.

2. The transgenic plant according to claim 1, wherein the light-inducible promoter is selected from the group consisting of a Rubisco promoter and a chlorophyll a/b-binding protein promoter.

3. The transgenic plant according to claim 1, wherein the plant is rice.

4. The transgenic plant according to claim 3, wherein the plant is a Basmati rice plant.

5. The transgenic plant according to claim 1, wherein the plant is a Basmati rice plant.

6. A transgenic monocot plant seed comprising a nucleic acid construct comprising:

a nucleic acid molecule encoding a light-labile, phytochrome A from *Arabidopsis;* a light-inducible promoter which is 5' to the nucleic acid molecule encoding a light-labile, phytochrome A; and a terminator region which is 3' to the nucleic acid molecule encoding a light-labile phytochrome A, wherein a plant grown from the transgenic monocot plant seed exhibits increased seed yield, as compared to a non-transgenic monocot plant of the same type.

7. The transgenic plant seed according to claim 6, wherein the light-inducible promoter is selected from the group consisting of a Rubisco promoter and a chlorophyll a/b-binding protein promoter.

8. The transgenic plant seed according to claim 6, wherein the plant is rice.

9. The transgenic plant seed according to claim 8, wherein the plant is a Basmati rice plant.

10. The transgenic plant seed according to claim 6, wherein the plant is a Basmati rice plant.

11. A method of increasing a monocot plant's seed yield, said method comprising:

providing transgenic monocot plants or transgenic monocot plant seeds comprising a nucleic acid construct comprising:

a nucleic acid molecule encoding a light-labile, phytochrome A;

a light-inducible promoter which is 5' to the nucleic acid molecule encoding a light-labile, phytochrome A; and a terminator region which is 3' to the nucleic acid molecule encoding a light-labile, phytochrome A; and growing the transgenic monocot plants or monocot plants grown from the transgenic monocot plant seeds, and selecting transgenic monocot plants that show an increase in the monocot plant's seed yield.

12. The method according to claim 11, wherein the nucleic acid molecule encoding a light-labile, phytochrome A is from a dicot.

13. The method according to claim 11, wherein the nucleic acid molecule encoding a light-labile, phytochrome A is from *Arabidopsis.*

14. The method according to claim 11, wherein the light-inducible promoter is selected from the group consisting of a Rubisco promoter and a chlorophyll a/b-binding protein promoter.

15. The method according to claim 11, wherein the plant is rice.

16. The method according to claim 15, wherein the plant is a Basmati rice plant.

17. The method according to claim 13, wherein the plant is a Basmati rice plant.

* * * * *